(12) United States Patent
Ganiger et al.

(10) Patent No.: US 10,704,734 B2
(45) Date of Patent: Jul. 7, 2020

(54) METHOD AND APPARATUS FOR DETERMINING LUBRICANT CONTAMINATION OR DETERIORATION IN AN ENGINE

(71) Applicant: General Electric Company, Schenectady, NY (US)

(72) Inventors: Ravindra Shankar Ganiger, Karnataka (IN); Anand Madihalli Srinivasan, Karnataka (IN); Uma Maheshwar Domala, Karnataka (IN); Thomas DeWitt Woodrow, Wyoming, OH (US)

(73) Assignee: General Electric Company, Schenectady, NY (US)

( * ) Notice: Subject to any disclaimer, the term of this patent is extended or adjusted under 35 U.S.C. 154(b) by 199 days.

(21) Appl. No.: 15/682,859

(22) Filed: Aug. 22, 2017

(65) Prior Publication Data

US 2019/0063678 A1 Feb. 28, 2019

(51) Int. Cl.
*F16N 29/00* (2006.01)
*G01N 33/28* (2006.01)
(Continued)

(52) U.S. Cl.
CPC ............. *F16N 29/00* (2013.01); *F01D 25/18* (2013.01); *F01M 11/10* (2013.01); *F02C 7/06* (2013.01);
(Continued)

(58) Field of Classification Search
CPC .... F01D 25/18; F01M 11/10; F01M 2011/14; F02C 7/06; F05D 2260/80; F16N 2200/02; F16N 2200/04; F16N 2200/20; F16N 2210/02; F16N 2210/08; F16N 2250/34; F16N 2260/18; F16N 29/00; F16N 29/04;
(Continued)

(56) References Cited

U.S. PATENT DOCUMENTS 6,170,318 B1 1/2001 Lewis
6,421,588 B1 7/2002 Janata
(Continued)

FOREIGN PATENT DOCUMENTS

CN 203347886 U 12/2013
EP 1 726 949 A1 11/2006
(Continued)

OTHER PUBLICATIONS

Extended European Search Report and Opinion issued in connection with corresponding EP Application No. 18189512.9 dated Jan. 28, 2019.
(Continued)

*Primary Examiner* — Maureen Wallenhorst
(74) *Attorney, Agent, or Firm* — McGarry Bair PC

(57) ABSTRACT

An apparatus and method for determining lubrication contamination or deterioration in an engine or a lubricant system of an engine can include at least one sensor provided in the lubricant system. The sensor can sense an aroma of a lubricant or the air around the lubricant to measure a chemical composition or an aromatic. The sensed chemical composition or aromatic can be compared to a baseline or threshold to determine a particular contamination type or deterioration level of the lubricant.

18 Claims, 7 Drawing Sheets

(51) Int. Cl.
  *F01D 25/18* (2006.01)
  *F16N 29/04* (2006.01)
  *F01M 11/10* (2006.01)
  *F02C 7/06* (2006.01)

(52) U.S. Cl.
  CPC ......... *F16N 29/04* (2013.01); *G01N 33/2888* (2013.01); *F01M 2011/14* (2013.01); *F05D 2260/80* (2013.01); *F16N 2200/02* (2013.01); *F16N 2200/04* (2013.01); *F16N 2200/20* (2013.01); *F16N 2210/02* (2013.01); *F16N 2210/08* (2013.01); *F16N 2250/34* (2013.01); *F16N 2260/18* (2013.01); *G01N 33/2835* (2013.01)

(58) Field of Classification Search
  CPC ............... G01N 33/28; G01N 33/2835; G01N 33/2888; G01N 33/30
  USPC .................. 436/60, 111, 120, 127, 164, 171
  See application file for complete search history.

(56) References Cited

U.S. PATENT DOCUMENTS

| | | | |
|---|---|---|---|
| 6,832,159 B2 | 12/2004 | Wakida et al. | |
| 6,842,234 B2 | 1/2005 | Kong et al. | |
| 7,531,137 B2 | 5/2009 | Uluyol | |
| 7,690,184 B2 | 4/2010 | Gauthier et al. | |
| 8,309,363 B2 | 11/2012 | Askins et al. | |
| 9,020,764 B2 | 4/2015 | Walte et al. | |
| 2005/0241989 A1* | 11/2005 | Sant | C10M 171/00 208/18 |
| 2015/0047419 A1 | 2/2015 | Cao et al. | |
| 2016/0109426 A1* | 4/2016 | Endou | G01N 33/2888 73/23.34 |
| 2019/0086382 A1* | 3/2019 | Inaba | F16C 33/6625 |

FOREIGN PATENT DOCUMENTS

| | | |
|---|---|---|
| JP | 0450639 A | 2/1992 |
| JP | 10-33343 A1 | 2/1998 |
| JP | 2003-107000 A | 4/2003 |
| JP | 2004069690 A | 3/2004 |
| WO | 2014/192912 A1 | 12/2014 |

OTHER PUBLICATIONS

Japanese Patent Office, First Office Action re Japanese Patent Application No. 2018-152832, dated Dec. 9, 2019, 11 pages, Japan.
Canadian Patent Office, Office Action re Canadian Patent Application No. 3,013,693, dated May 3, 2019, 5 pages.

* cited by examiner

METHOD AND APPARATUS FOR DETERMINING LUBRICANT CONTAMINATION OR DETERIORATION IN AN ENGINE

BACKGROUND OF THE INVENTION

Turbine engines, and particularly gas or combustion turbine engines, are rotary engines that extract energy from a flow of combusted gases passing through the engine onto a multitude of rotating turbine blades.

Gas turbine engines utilize a lubricant system for temperature control and lubrication of the engine during operation. Often, heightened temperatures of the lubricant can lead to oil slag, varnish or coking, which can reduce effectiveness of the oil or can clog or damage portions of the engine. Similarly, the lubricant can become contaminated, which can also reduce effectiveness or damage the engine.

Typically, the lubricant is periodically changed, but may not be changed based upon present need of the engine or lubricant. As such, the lubricant may spend too great a time in the engine without being changed. Often, during inspection, an inspector smells the lubricant for a determination of quality, such as burning to determine present lubricant quality. This method is not effective, accurate, or safe.

BRIEF DESCRIPTION OF THE INVENTION

In one aspect, the disclosure relates to a method for determining contamination in vehicle lubrication system including: sensing an aroma of a lubricant in the vehicle lubrication system with at least one sensor; generating a signal, from the at least one sensor, representative of the aroma; and determining, with a controller, a contamination or a deterioration of the lubricant based on the signal representative of the aroma.

In yet another aspect, the disclosure relates to an aircraft including an engine and a lubricant flow system fluidly coupled to the engine and containing lubricant therein. At least one lubrication sensor is included for outputting an aroma signal related to an aroma in at least a portion of one of the engine or the lubricant flow system. A controller is configured to compare the aroma signal to a stored signal, determine a contamination or deterioration based upon the aroma signal, and output an indication representative of the determined contamination or deterioration.

DETAILED DESCRIPTION OF THE INVENTION

Figure 1:
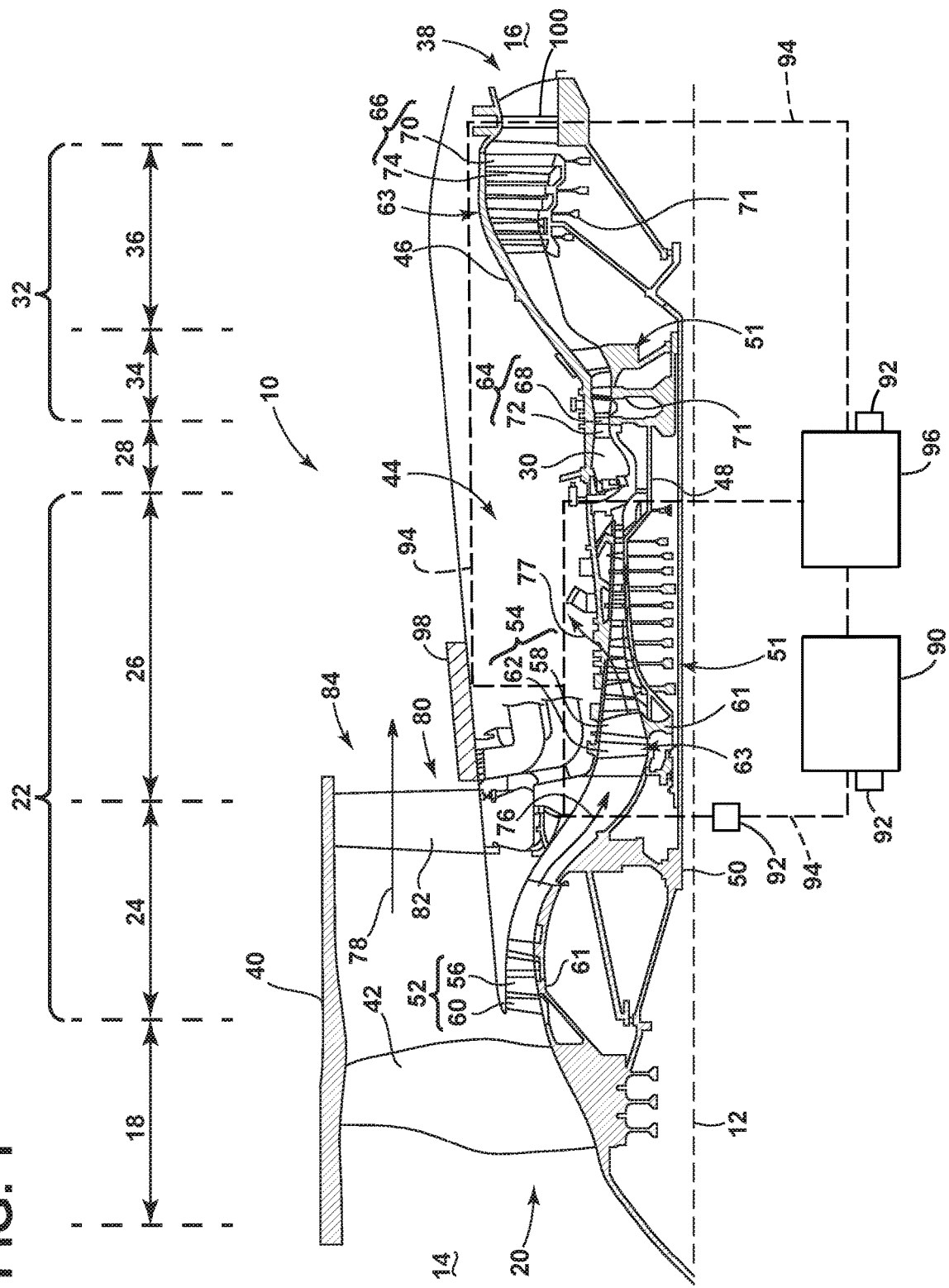
FIG. 1 is a schematic cross-sectional diagram of a gas turbine engine for an aircraft including a lubricant flow system.

Aspects of the disclosure described herein are directed to a method and apparatus for sensing and measuring aspects of lubricant within a turbine engine. Measurements can be made within the engine in real time, as well as between operations and while the engine is on-wing. The real-time measurements can provide for a multitude of readings for different aspects of the lubricant. The different readings can be interpreted and compared against baseline or threshold values to determine different types of contamination for the lubricants, which can provide for improved maintenance and can minimize the negative effects of lubricant contamination. For purposes of illustration, the present disclosure will be described with respect to a gas turbine engine for an aircraft. It will be understood, however, that aspects of the disclosure described herein are not so limited and can have general applicability within a lubricant flow system in an engine for a vehicle, including compressors, as well as in non-aircraft applications, such as other mobile applications and non-mobile industrial, commercial, and residential applications. Other vehicles other than aircraft are contemplated, such as mobile land, air, or sea vehicles.

As used herein, the term "forward" or "upstream" refers to moving in a direction toward the engine inlet, or a component being relatively closer to the engine inlet as compared to another component. The term "aft" or "downstream" used in conjunction with "forward" or "upstream" refers to a direction toward the rear or outlet of the engine or being relatively closer to the engine outlet as compared to another component. Additionally, as used herein, the terms "radial" or "radially" refer to a dimension extending between a center longitudinal axis of the engine and an outer engine circumference. Furthermore, as used herein, the term "set" or a "set" of elements can be any number of elements, including only one.

All directional references (e.g., radial, axial, proximal, distal, upper, lower, upward, downward, left, right, lateral, front, back, top, bottom, above, below, vertical, horizontal, clockwise, counterclockwise, upstream, downstream, forward, aft, etc.) are only used for identification purposes to aid the reader's understanding of the present disclosure, and do not create limitations, particularly as to the position, orientation, or use of aspects of the disclosure described herein. Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to one another. The exemplary drawings are for purposes of illustration only and the dimensions, positions, order and relative sizes reflected in the drawings attached hereto can vary.

Referring to FIG. 1, an engine 10 has a generally longitudinally extending axis or centerline 12 extending forward 14 to aft 16. The engine 10 includes, in downstream serial flow relationship, a fan section 18 including a fan 20, a compressor section 22 including a booster or low pressure (LP) compressor 24 and a high pressure (HP) compressor 26, a combustion section 28 including a combustor 30, a turbine section 32 including a HP turbine 34, and a LP turbine 36, and an exhaust section 38.

The fan section 18 includes a fan casing 40 surrounding the fan 20. The fan 20 includes a plurality of fan blades 42 disposed radially about the centerline 12. The HP compressor 26, the combustor 30, and the HP turbine 34 form a core 44 of the engine 10, which generates combustion gases. The core 44 is surrounded by core casing 46, which can be coupled with the fan casing 40.

A HP shaft or spool 48 disposed coaxially about the centerline 12 of the engine 10 drivingly connects the HP turbine 34 to the HP compressor 26. A LP shaft or spool 50, which is disposed coaxially about the centerline 12 of the engine 10 within the larger diameter annular HP spool 48, drivingly connects the LP turbine 36 to the LP compressor 24 and fan 20. The spools 48, 50 are rotatable about the engine centerline and couple to a plurality of rotatable elements, which can collectively define a rotor 51.

The LP compressor 24 and the HP compressor 26 respectively include a plurality of compressor stages 52, 54, in which a set of compressor blades 56, 58 rotate relative to a corresponding set of static compressor vanes 60, 62 (also called a nozzle) to compress or pressurize the stream of fluid passing through the stage. In a single compressor stage 52, 54, multiple compressor blades 56, 58 can be provided in a ring and can extend radially outwardly relative to the centerline 12, from a blade platform to a blade tip, while the corresponding static compressor vanes 60, 62 are positioned upstream of and adjacent to the rotating blades 56, 58. It is noted that the number of blades, vanes, and compressor stages shown in FIG. 1 were selected for illustrative purposes only, and that other numbers are possible.

The blades 56, 58 for a stage of the compressor mount to a disk 61, which mounts to the corresponding one of the HP and LP spools 48, 50, with each stage having its own disk 61. The vanes 60, 62 for a stage of the compressor mount to the core casing 46 in a circumferential arrangement.

The HP turbine 34 and the LP turbine 36 respectively include a plurality of turbine stages 64, 66, in which a set of turbine blades 68, 70 are rotated relative to a corresponding set of static turbine vanes 72, 74 (also called a nozzle) to extract energy from the stream of fluid passing through the stage. In a single turbine stage 64, 66, multiple turbine blades 68, 70 can be provided in a ring and can extend radially outwardly relative to the centerline 12, from a blade platform to a blade tip, while the corresponding static turbine vanes 72, 74 are positioned upstream of and adjacent to the rotating blades 68, 70. It is noted that the number of blades, vanes, and turbine stages shown in FIG. 1 were selected for illustrative purposes only, and that other numbers are possible.

The blades 68, 70 for a stage of the turbine can mount to a disk 71, which is mounts to the corresponding one of the HP and LP spools 48, 50, with each stage having a dedicated disk 71. The vanes 72, 74 for a stage of the compressor can mount to the core casing 46 in a circumferential arrangement.

Complementary to the rotor portion, the stationary portions of the engine 10, such as the static vanes 60, 62, 72, 74 among the compressor and turbine section 22, 32 are also referred to individually or collectively as a stator 63. As such, the stator 63 can refer to the combination of non-rotating elements throughout the engine 10.

In operation, the airflow exiting the fan section 18 splits such that a portion of the airflow is channeled into the LP compressor 24, which then supplies pressurized air 76 to the HP compressor 26, which further pressurizes the air. The pressurized air 76 from the HP compressor 26 mixes with fuel in the combustor 30 where the fuel combusts, thereby generating combustion gases. The HP turbine 34 extracts some work from these gases, which drives the HP compressor 26. The HP turbine 34 discharges the combustion gases into the LP turbine 36, which extracts additional work to drive the LP compressor 24, and the exhaust gas is ultimately discharged from the engine 10 via the exhaust section 38. The driving of the LP turbine 36 drives the LP spool 50 to rotate the fan 20 and the LP compressor 24.

A portion of the pressurized airflow 76 can be drawn from the compressor section 22 as bleed air 77. The bleed air 77 can be drawn from the pressurized airflow 76 and provided to engine components requiring cooling. The temperature of pressurized airflow 76 entering the combustor 30 is significantly increased. As such, cooling provided by the bleed air 77 is necessary for operating of such engine components in the heightened temperature environments.

A remaining portion of the airflow 78 bypasses the LP compressor 24 and engine core 44 and exits the engine assembly 10 through a stationary vane row, and more particularly an outlet guide vane assembly 80, comprising a plurality of airfoil guide vanes 82, at the fan exhaust side 84. More specifically, a circumferential row of radially extending airfoil guide vanes 82 are utilized adjacent the fan section 18 to exert some directional control of the airflow 78.

Some of the air supplied by the fan 20 can bypass the engine core 44 and be used for cooling of portions, especially hot portions, of the engine 10, and/or used to cool or power other aspects of the aircraft. In the context of a turbine engine, the hot portions of the engine are normally downstream of the combustor 30, especially the turbine section 32, with the HP turbine 34 being the hottest portion as it is directly downstream of the combustion section 28. Other sources of cooling fluid can be, but are not limited to, fluid discharged from the LP compressor 24 or the HP compressor 26.

An exemplary vehicle lubrication system is illustrated as a lubricant flow system 88 arranged throughout the engine 10. A lubricant reservoir 90 can contain a volume of lubricant to pass along the lubricant flow system 88. A series of lubricant conduits 94 can interconnect multiple elements of the lubricant flow system 88 providing for provision of the lubricant throughout the lubricant flow system.

A first heat exchanger 96 can be included in the lubricant flow system 88. The first heat exchanger 96 can include a fuel/lubricant heat exchanger or an oil/lubricant heat exchanger in non-limiting examples. A fuel/lubricant heat exchanger can be used to heat or cool engine fuel with lubricant passing through the first heat exchanger. A lubricant/oil heat exchanger can be used to heat or cool additional lubricants passing within the engine 10, fluidly separate from the lubricant passing along the lubricant flow system 88. In one example, the lubricant/oil heat exchanger can be a servo/lubricant heat exchanger.

A second heat exchanger 98 can be provided along the exterior of the engine core 44, downstream of the outlet guide vane assembly. The second heat exchanger 98 can be an air/lubricant heat exchanger, for example, adapted to convectively cool lubricant in the lubricant flow system 88 utilizing the airflow passing through the outlet guide vane assembly 80.

The conduit 94 extending between the first heat exchanger 96 and the second heat exchanger 98 can pass through a conduit 100 extending through a strut in the aft portion of the engine 10.

It should be understood that the organization of the lubricant flow system 88 as shown is by way of example only to illustrate an exemplary system within the engine 10 for circulating lubricant for purposes such as lubrication or heat transfer. Any organization for the lubricant flow system 88 is contemplated, with or without the elements as shown, or including additional elements interconnected by any necessary conduit system.

One or more sensors 92 can be included in the lubricant flow system 88. By way of non-limiting example, a sensor 92 has been illustrated as being provided on the lubricant reservoir. Sensors 92 can be positioned anywhere along the lubricant flow system 88, such as along the lubricant conduits 94, or on any element forming part of the lubricant flow system 88. The sensors 92 can be any suitable sensors including, but not limited to, aroma sensors adapted to measure the smell or aroma of the lubricant in order to determine the composition of the lubricant or determine the formation of new chemicals within the lubricant resultant of a change to the lubricant such as deterioration or contamination. Alternatively, it is contemplated that the sensors 92 can be any suitable sensor to measure the chemical composition of the lubricant. Non-limiting examples of suitable sensors can include Raman Spectroscopy, X-Ray spectroscopy, infrared sensors, laser sensors, olfactometers, or moisture detectors. Such measurements can include, but are not limited to, fuel in the lubricant or fuel vapor, fuel dilution, oil coking, oil varnishing, oil slag, free-on-board oil, Sulphur, moisture or water, sulphides, hydrogen sulfide, thiols, alcohols, carboxylic acids, aldehydes, ketones, oxides, olefins, alkanes, nitrides, cycloalkanes, aromatics, asphaltenes, silicates, amines, esters, phenolics, or metallics. Fuel, fuel vapor, or fuel dilution can all be representative of the existence of fuel leaking into the lubricant. Oil coking is the generation of solid oil residue due to severe oxidation and thermal breakdown of the lubricant, typical to extreme engine temperatures. Oil varnishing can results in generation of lubricant byproducts due to oxidation or thermal stressing of the lubricant, similar to that of oil coking. Oil slag can be the buildup of lubricant that has broken down, which can lead to corrosion, resultant of extreme heating of the lubricant. Free-on-board oil can be an external oil source that becomes intermixed with the lubricant. All of which are examples of at least a portion of an aroma that can be given off by lubricant in the lubricant flow system 88. Particular, exemplary aromatics that can give off an aroma and be sensed by the sensor can further include warm, tingling, itching, metallic, cool, sharp, pungent, hot, roast, moist, cold, tar-like, slurry, smoke, or burning aromatics. Additional contaminants that can be suitable for identification by the sensors can include dirt, dust, water, sand, ice, organic material, or other common engine contaminants. Furthermore, contaminants such as foreign objects or debris such as eroded metals, ceramics or particles from other parts of the engine or contaminants resultant of wear on the engine can be suitable for identification by the sensors. Additional sensors such as flow meters, temperature sensors, timers, or pressure sensors can be used to detect lubricant leakage, lubricant age, or operational temperature, in addition to the sensors configured to determine or sense an aroma described above.

Figure 2:
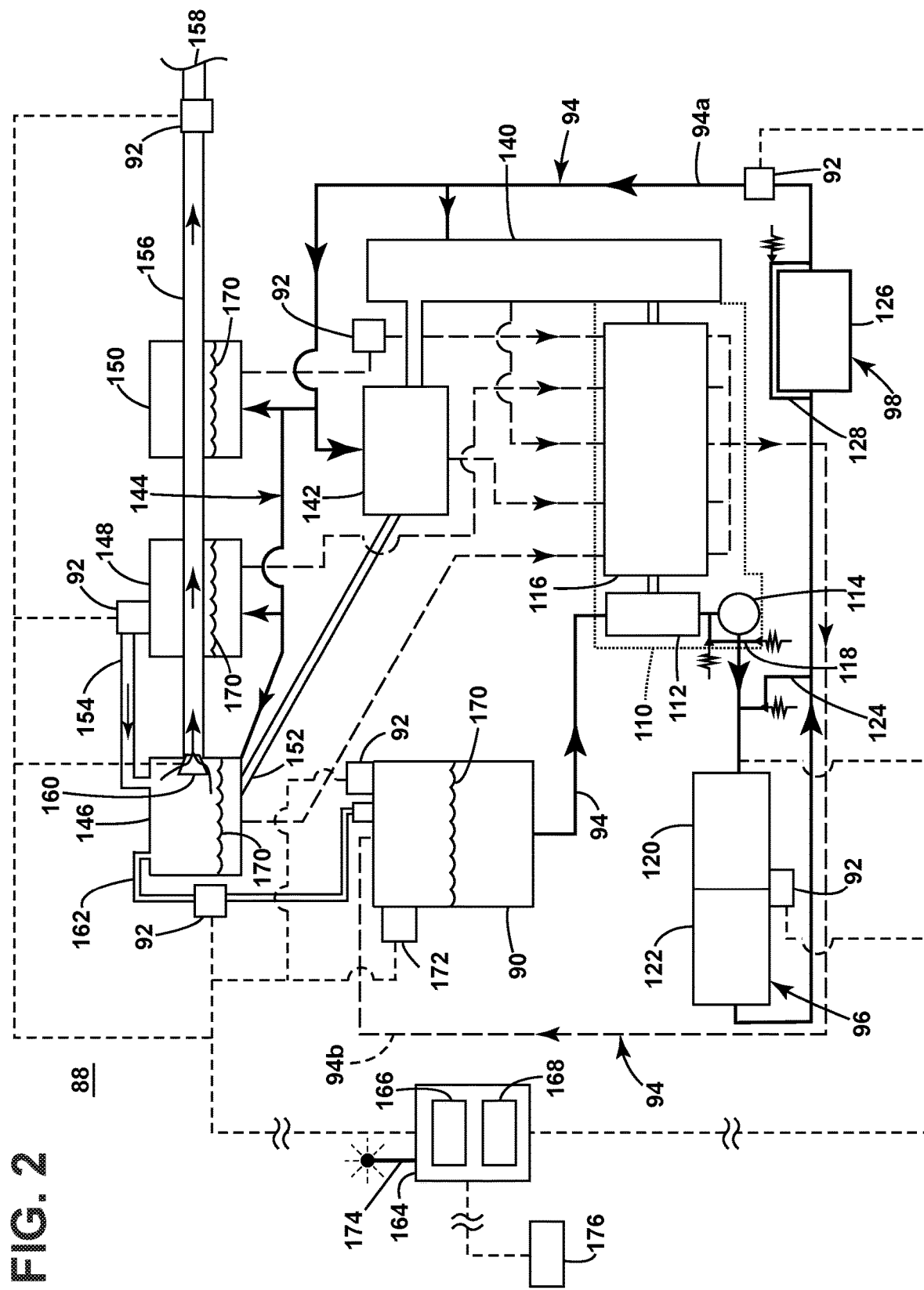
FIG. 2 is a schematic of the engine lubricant flow system of FIG. 1 including sensors positioned along the lubricant flow system.

Referring now to FIG. 2, an exemplary schematic for the lubricant flow system 88 better illustrates different exemplary elements forming the lubricant flow system 88, as well as exemplary positions for sensors 92 along the lubricant flow system 88. The lubricant conduits 94 can be separated into cool lubricant conduits 94a and hot lubricant conduits 94b, shown in solid-line and dashed-line, respectively. The different types of conduits are reflective of exemplary lubricant temperatures in different areas of the lubricant flow system 88, but should not be limiting of the particular lubricant flow system 88. Such temperatures are exemplary and actual organizations or local temperatures can differ. The arrows along the lubricant conduits 94 illustrate exemplary flow direction, while flow direction can vary among different lubricant flow systems.

A lube and scavenge pump system 110 can couple to the lubricant reservoir 90 by one lubricant conduit 94. A pump 112 within the lube and scavenge pump 110 can couple to the lubricant reservoir 90 directly. A filter 114 can be provided downstream of the pump 112. A scavenge manifold 116 can be included in the lube and pump system 110. The scavenge manifold 116 can couple to the lubricant reservoir 90 with the lubricant conduit 94 for returning a volume of lubricant to the lubricant reservoir 90. A first recirculation conduit 118 can be positioned downstream of the filter 114 for recirculating lubricant upstream of the filter 114.

The first heat exchanger 96 can be arranged downstream of the lube and scavenge pump system 110. A lubricant/oil heat exchanger 120 and a fuel/lubricant heat exchanger 122 can be included in the first heat exchanger 96. A second recirculation conduit 124 can be provided downstream of the first heat exchanger 96 for recirculating lubricant through the first heat exchanger 96.

The second heat exchanger 98 can be positioned downstream of the first heat exchanger 96, and can be an air/lubricant heat exchanger 126 to cool lubricant via convective heat exchange with a flow of air through the engine 10. A third recirculation conduit 128 can be provided at the second heat exchanger 98 to recirculate a volume of lubricant through the second heat exchanger 98.

A first gearbox 140, a second gearbox 142, and a sump system 144 can couple to the lubricant supply downstream of the second heat exchanger 98. Provision of lubricant to each of the aforementioned can be controlled with a valve, for example. The first gearbox 140 can be an accessory gearbox, in one example. The second gearbox 142 can be a transfer gearbox, and can couple to the accessory gearbox 140. The first and second gearboxes 140, 142 can couple to the scavenge manifold 116 via lubricant conduits 94.

The sump system 144 can be a bearing sump region for lubricating engine bearings, in one non-limiting example. A first sump 146, a second sump 148, and a third sump 150 can be included in the sump system 144. While three sumps are illustrated, any number of sumps is contemplated. In one example, a valve can control provision of lubricant to any one of the sumps. Each of the first, second, and third sumps 146, 148, 150 can fluidly couple to the scavenge manifold 116 via lubricant conduits 94. A first vent 152 can extend from the first sump 146 to the second gearbox 142 for venting any air to the first sump 146. A second vent 154 can couple the second sump 148 to the first sump 146, for venting excess air among the sumps 146, 148.

An exhaust line 156 can extend from the first sump 146 to an outlet 158, providing for exhausting any lubricant or gas from the lubricant flow system 88. Such exhausting can be overboard, for example. A valve 160 can be provided on the exhaust line 156 to selectively open or close the exhaust line 156. A third vent 162 can extend from the first sump 146 to the lubricant reservoir 90, providing for venting air to or from the lubricant reservoir 90.

In operation, the lubricant reservoir 90 can be filled with a volume of lubricant 170, which can be distributed about the lubricant flow system 88. From the lubricant reservoir 90, the lubricant 170 can pass through one conduit 94 to the lube and scavenge pump system 110, driven by the pump 112. The lubricant 170 can be provided through the filter 114, and can optionally be recirculated through the filter 114 by the first recirculation conduit 118 as is desirable to remove any excess particulate matter within the lubricant 170.

The lubricant 170 can then pass to the first heat exchanger 96, which can be used to cool the fuel or other lubricant. The second recirculation conduit 124 can be used to recirculate the lubricant 170 through the first heat exchanger 96.

The lubricant 170 can then pass to the second heat exchanger 98 where the lubricant 170 can be cooled by the air/lubricant heat exchanger 126. The third recirculation conduit 128 can recirculate the lubricant 170 through the second heat exchanger 98 to further cool the lubricant 170.

The lubricant 170 can then pass the first and/or second gearbox 140, 142 to cool or lubricate the first and/or second gearboxes 140, 142. From the first or second gearboxes 140, 142, the scavenge manifold 116 can return the lubricant 170 to the lubricant reservoir 90. Alternatively, the lubricant 170 can pass from the second heat exchanger 98 to the sump system 144, where the lubricant 170 can be provided to one or more of the sumps 146, 148, 150. Lubricant 170 within the sump system 144 can be returned to the lubricant reservoir 90 via the scavenge manifold 116 and the pump 112 within the lube and scavenge pump system 110. Lubricant 170 in the first sump 146 can be selectively exhausted overboard by opening the valve 160 and permitting air or lubricant to pass through the outlet 158 of the exhaust line 156. Additionally, the third vent 162 can provide for exhausting air or relieving pressure within the lubricant reservoir 90 through the first sump 146.

It should be understood that the lubricant flow system 88 is a fluid recirculation system for selectively cooling or lubricating portions of the engine 10 by selectively providing a volume of lubricant throughout the lubricant flow system 88. While there are seven sensors 92 positioned within the lubricant flow system 88 in FIG. 2, it should be appreciated that any number of sensors 92 can be used in any position. Some positions or organizations can be preferable for making particular measurements or for determining sources of contamination. For example, the sensor 92 position downstream of the second heat exchanger 98 can be beneficial in determining contamination entering the lubricant 170 at the second heat exchanger 98.

FIG. 2 again illustrates that one or more sensors 92 can be positioned at various locations about the lubricant flow system 88. As illustrated, exemplary sensors 92 are positioned on the lubricant reservoir 90, the first heat exchanger 96, downstream of the second heat exchanger 98, along one lubricant conduit 94 between the third sump 150 and the scavenge manifold 116, at the second sump 148, along the third vent 162, and along the exhaust line 156, while any suitable location is contemplated. The sensor 92 mounted to the lubricant reservoir 90 can sense an aroma for stored lubricant 170, as well as measure a baseline aroma prior to operation of the lubricant flow system 88. Additionally, the sensor 92 on the lubricant reservoir 90 can measure changes to the lubricant 170 through use of the lubricant and operation of the lubricant flow system 88.

One sensor 92 can mount to the first heat exchanger 96 to measure the lubricant passing through one or both of the lubricant/oil heat exchanger 120 and the fuel/lubricant heat exchanger 122. The sensor 92 positioned downstream of the second heat exchanger 98 can be used to determine contamination at the second heat exchanger 98. The sensor on the conduit 94 between the third sump 150 and the scavenge manifold 116, as well as the sensor 92 on the second sump 148, can be used to measure lubricant 170 that has passed through the lubricant flow system 88. The sensor 92 provided on the exhaust line 156 can measure the lubricant 170 exhausted from the lubricant flow system 88. The sensor 92 positioned along the third vent 162 can be used to measure the aroma of the lubricant 170 exhausting from the lubricant reservoir 90.

An injector 172 can be provided in the lubricant flow system 88. In one non-limiting example, the injector 172 can be provided at the lubricant reservoir 90, while any position is contemplated. Preferably, the injector 172 is located along the lubricant flow system 88 adjacent a sensor 92. While such a location is not required the injector 172 is preferably upstream of at least one sensor 92. The injector 172 can provide for selectively injecting gaseous, fluid, or solid chemicals into the lubricant reservoir 90. The injector 172 can be adapted to inject a particular chemical into the lubricant to be identified by the sensors 92 or to react in a particular way with the lubricant or the fluid or vapor in the lubricant flow system 88. The injector 172 can be in communication with the controller 164. The controller 164 can operate the injector 172 to inject material into the lubricant flow system 88 at desired times, locations, or in desired amounts. Such an injection can be controlled to coincide with particular measurements by the sensor 92.

Optionally, the injector 172 can inject a chemistry into the lubricant 170 at the lubricant reservoir 90. The sensors 92 can measure the lubricant 170 and make a determination of contamination based on injected material. For example, a reduced concentration of the injected chemistry can represent a leakage or volume contamination of the lubricant 170. In one example, the injector 172 can inject sulfur. The sulfur can react with the lubricant to form hydrogen sulfide or thiols, which can generate a different aroma. In another example, the injector 172 can inject alcohols or carboxylic acids, which can give rise to different esters, where each ester can have a unique aroma based upon the particular alcohol or carboxylic acid. In yet another example, the injector 172 can be used to inject aldehydes and ketones to form aromatic aldehydes, which have stronger odors. Such aldehydes and ketones can improve aromatic detection by the sensors 92.

A controller 164 can be communicatively and operably coupled to the sensors 92. Additionally, the controller 164 can be communicatively and operably coupled with other portions of the lubricant flow system 88, such as the pump 112 and valve 160 in non-limiting examples. The controller 164 can be adapted to continuously monitor the sensor 92. Such continuous monitoring can include continuously comparing sensor measurements, determining data, aromas, contaminations, or deteriorations, or outputting data in real time. Continuously can include being continuous, or being at set intervals. The controller 164 can control operation of the lubricant flow system 88. The controller 164 can be located locally, within the engine 10 at the lubricant flow system 88, or can be located remotely. In a first example, the controller 164 can be located within an aircraft control area, such as a cockpit. In this example, the controller 164 can be physically coupled to the sensors 92 and the lubricant flow system 88, or can be adapted to communicate remotely over a short distance. A wireless communication link 174 on the controller 164 can permit wireless communication. Alternatively, in a second example, the controller 164 can be located remotely at a control area, such as a communication center in communication with the aircraft from the ground. In such a setup, the controller 164 can communicate wirelessly with the control area. The controller 164 can also be connected with other controllers of the engine 10 or vehicle. Furthermore, the controller 164 can be remote. For example, the controller 164 can be a wireless or remote handheld device that is in wireless communication with one or more sensors 92. In such an example, the controller 164 could be a wireless, handheld device that uses near field communication (NFC) to read sensor measurements during engine maintenance, to determine any contamination or deterioration. In another example, the controller 164 could be positioned remotely of the sensors 92, but in wireless communication with the sensors to make real-time measurements of the sensors 92. As such, any suitable wireless communication network between the sensors 92 and the controller 164 is contemplated such that communication between the two is achieved. In such an organization, the sensors 92 can include wireless capabilities, such as including a transmitter, enabling wireless communication with the controller 164.

The controller 164 can include a memory 168. The memory 168 can include random access memory (RAM), read-only memory (ROM), flash memory, or one or more different types of portable electronic memory, such as discs, DVDs, CD-ROMs, etc., or any suitable combination of these types of memory. The controller 164 can include one or more processors 166, which can be running any suitable programs.

A computer searchable database of information can be stored in the memory 168 and accessible by processor 166. The processor 166 can run a set of executable instructions to access the database. Alternatively, the controller 164 can be operably coupled to a database of information accessible by the processor 166. For example, such a database can be stored on an alternative computer or controller. It will be understood that the database can be any suitable database, including a single database having multiple sets of data, multiple discrete databases linked together, or even a simple table of data. It is contemplated that the database can incorporate a number of databases or that the database can actually be a number of separate databases.

The database can store data that can include historical data related to the lubricant, sensors 92, or measurements thereof, including previous sensor measurements. The database can also include reference values including predetermined values for the lubricant or the aroma of the lubricant including when the lubricant is new or unused, or for a particular type, chemical composition, or brand of lubricant. For example, the predetermined values can be baseline values for measured aromas, threshold values such as maximum or minimum values for particular measured aromas, or other measurements. The database an also include reference values including predetermined lubricant deterioration percentages or a multitude of contamination types. For example, the database can include data representative of a lubricant deterioration level suggesting a lubricant change is needed. In another example, the database can include data representative of a fuel contamination in the lubricant.

Alternatively, it is contemplated that the database can be separate from the controller 164 but can be in communication with the controller 164 such that it can be accessed by the controller 164. For example, it is contemplated that the database can be contained on a portable memory device and in such a case, and can include a port 196 (FIG. 3) for receiving the portable memory device and such a port would be in electronic communication with the controller 164 such that controller 164 can read the contents of the portable memory device. It is also contemplated that the database can be updated through the wireless communication link 174 in communication with the controller 164. Further, it is contemplated that such a database can be located off the aircraft or engine 10 at a location such as airline operation center, flight operations department control, or another location. The controller 164 can be operably coupled to a wireless network over which the database information can be provided to or from the controller 164.

The controller 164 can further include all or a portion of a computer program having an executable instruction set for recording or analyzing data in the form of a signal generated by the sensors 92. Such recordation or analytics can include comparing measurements to historical database information to determine a contamination or deterioration of the lubricant. The program can include a computer program product that can include machine-readable media for carrying or having machine-executable instructions or data structures stored thereon. Such machine-readable media can be any available media, which can be accessed by a general purpose or special purpose computer or other machine with a processor. Generally, such a computer program can include routines, programs, objects, components, data structures, algorithms, etc. that have the technical effect of performing particular tasks or implement particular abstract data types. Machine-executable instructions, associated data structures, and programs represent examples of program code for executing the exchange of information as disclosed herein. Machine-executable instructions can include, for example, instructions and data, which cause a general-purpose computer, special purpose computer, or special-purpose processing machine to perform a certain function or group of functions.

A display 176 can be operably coupled to controller 164. The display 176 can be coupled wirelessly or directly to the controller 164 for displaying data from the databases, or data representative of measurements made by the sensors 92, or signals generated from the sensors 92. The display 176 can be located in on the aircraft carrying the engine 10, such as in the cockpit where it can be viewed by pilots or other aircraft operators or maintenance crew. Such a display 176 within the aircraft can permit real-time monitoring of measurements made by the sensors 92. Alternatively, the display 176 can be located remotely, such as at the airline operation center, flight operations department control, or another location. Such a remote position for the display 176 can provide for real-time monitoring of the measurements of the sensors 92 remotely from the engine 10 and aircraft. Additionally, the display 176 can be a mobile display, which can be used locally during maintenance of the engine 10, for example.

Figure 3:
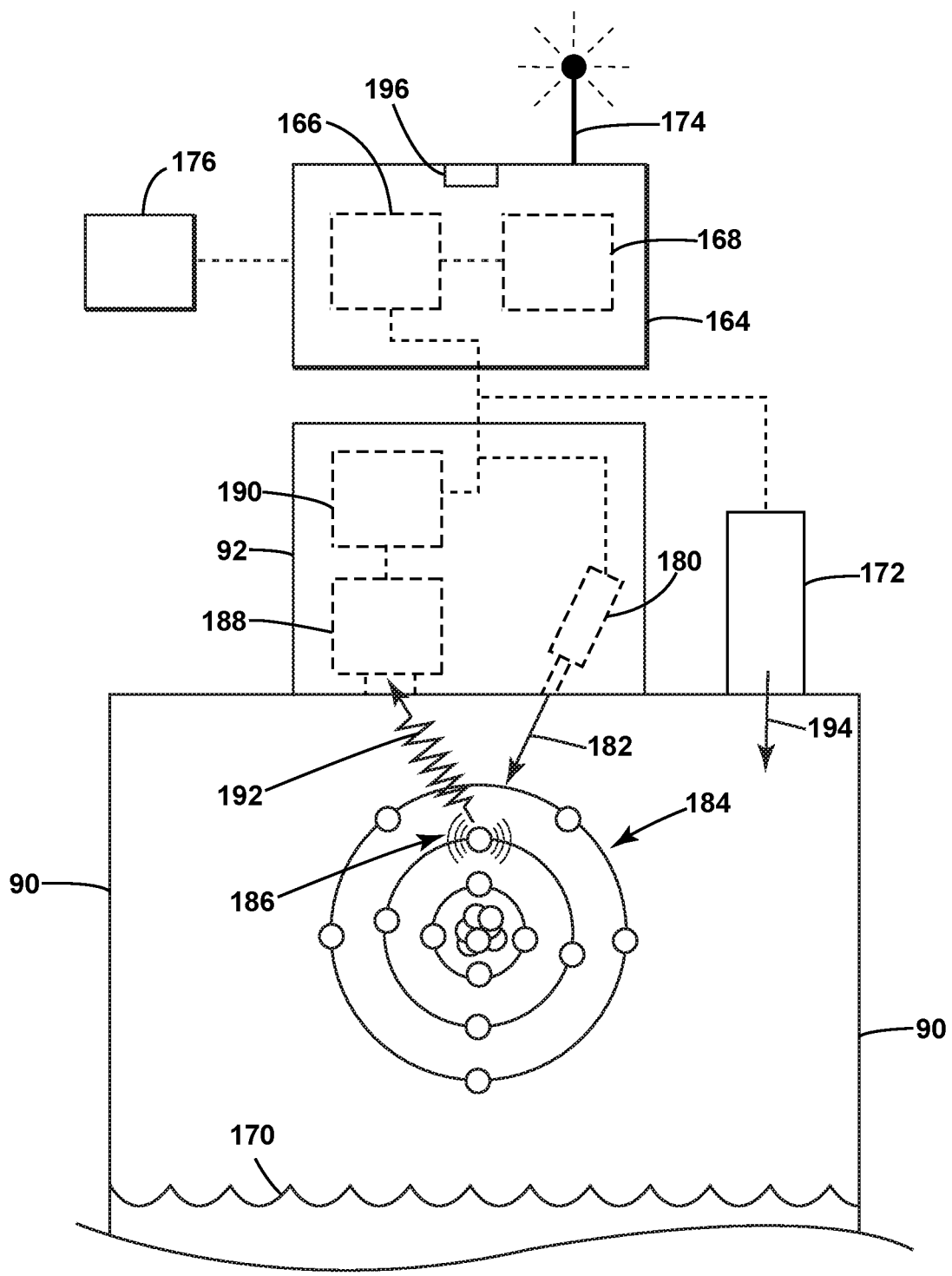
FIG. 3 is a schematic view of one sensor of FIG. 2 sensing the aroma of lubrication in the lubricant flow system and communicating with a controller.

Referring now to FIG. 3, a top portion of the lubricant reservoir 90 is shown including one mounted sensor 92 and one mounted injector 172. The sensor 92 can be a Raman spectrometer, for example. The sensor 92 can include an output source 180, for emitting light radiation 182. A detector 188 can be included, coupled to a digital processor 190 for detecting the light radiation 182 and processing the detection, respectively. The digital processor 190 and the output sources 180 can be couple to the controller 164. Operation of the sensor 92 can be controlled by the controller 164 and a measured signal can be received at the processor 166 from the digital processor 190. The wireless communication link 174 can be provided on the controller 164 for wirelessly communicating the measured signal. Additionally, a port 196 can be included on the controller 164 for communicating to and from the controller 164. The port 196 can be adapted to receive input at the controller 164, such as a wired connection with a removable adapter, such as removable memory.

In operation of the sensor 92 by the controller 164, the processor 166 can send a signal to the sensor 92 to make a measurement. The output source 180 emits light radiation 182, such as a laser, to interact with vibrations 186 of the aroma molecule 184, to cause light scattering 192. The detector 188 can be used to detect the light scattering 192 that is scattered from the aroma molecule 184. The digital processor 190 can generate a signal representative of the detected light scattering 192.

The signal generated by the digital processor 190 can be communicated to the controller 164 where it is received by the processor 166. The processor 166 can interpret the signal and analyze the signal by any suitable method. For example, the processor 166 can compare the signal with data stored in the memory 168, such as comparison with a baseline aroma measurement, or with minimum or maximum threshold values. Such comparisons can be used to determine contaminations or deteriorations of the lubricant represented in the aroma molecule 184.

Optionally, the injector 172 can inject a chemical 194 into the lubricant 170 or the air around the lubricant to interact with the aroma molecule 184. Detection by the sensor 92 can be facilitated by the injector 172, which can provide for improved detection, or particularized detection of a certain type of contaminant or type of deterioration. In one example, the injector 172 can inject the chemical 194 to react with the aroma molecule 184 to form a new aroma molecule (not shown) that is more readily detectable by the sensor 92 or particularized to a type of contamination. For example, the injector 172 could inject a chemical 194 adapted to produce an aroma indicative of a particular type of contamination. For example, the injector could inject a chemical 194 that interacts with the aroma molecule 184 if it is formed by a fuel contamination. Such an interaction could make the molecule 184 more readily detectable by the detector 188.

Figure 4:
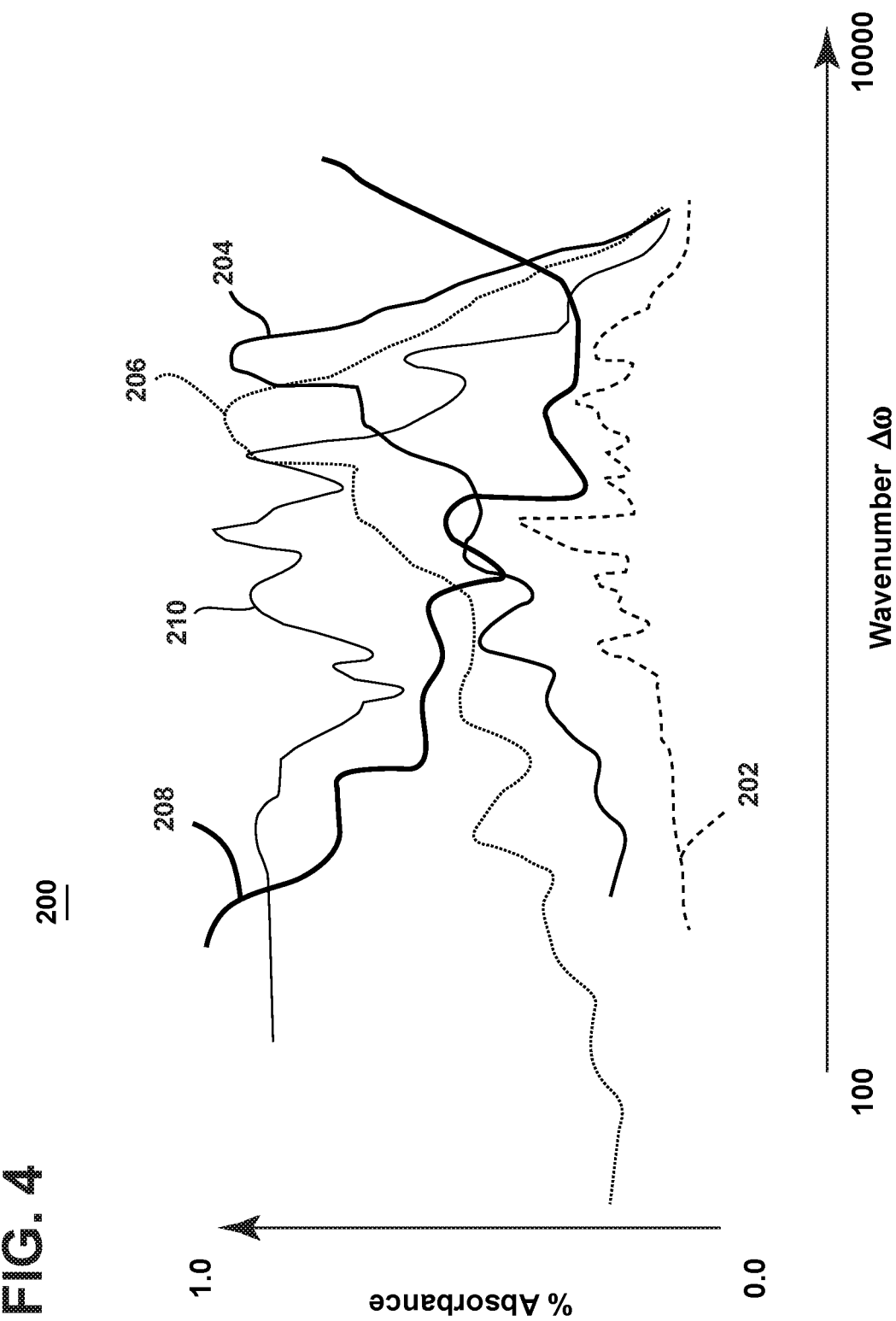
FIG. 4 is a plot graph including a plot showing baseline lubricant absorbance and three additional plots showing data analysis identifying differing lubricant states based upon measurements from the sensors of FIG. 3.

Referring now to FIG. 4, an exemplary plot graph 200 illustrates a measurement spectrum made by an exemplary sensor 92 using Raman Spectroscopy. The plot graph 200 can be representative of a chemical analysis as a structural fingerprint, signature, or profile of the lubricant 170 determined by measuring excitation including vibrational, rotational, or low-frequency modes in the lubricant 170 by the sensors 92. The plot graph 200 illustrates five plots as a baseline plot 202 representative of good or new lubricant, a first deterioration plot 204 representing 20-40% lubricant deterioration, a second deterioration plot 206 representing 40-60% deterioration, an oil slag or varnish plot 208, and an oil coking plot 210. The plots 202-210 are plotted by percentage of absorbance against wavenumber $\Delta\omega$, which can be representative of the Raman shift defined by:

$$\Delta\omega = \left(\frac{1}{\lambda_0} - \frac{1}{\lambda_1}\right) \quad (1)$$

where $\lambda_0$ is the excitation wavelength and $\lambda_1$ is the Raman spectrum wavelength.

The baseline plot 202 can be a baseline signature of the lubricant 170, which can be made as an initial measurement of lubricant by the sensor, which can represent good or new lubricant. The sensor 92 of FIG. 2 provided on the lubricant reservoir 90 can be used to determine the baseline plot 202, while the use of any suitable sensor 92 is contemplated. Such a baseline measurement can be sent to the controller 164 to be stored and used for comparison for later measurements by the sensor 92 or other sensors 92 within the system. In one example, the baseline plot 202 can be measured prior to each engine operation. Alternatively, such as a standard baseline signature can be used for new, unused lubricant after change of the lubricant. The baseline plot 202 can be stored in the memory 168 of the controller 164 for comparison with future measurements from the sensors 92, such as real-time measurements during operation of the engine 10. As such, the signature in the baseline plot 202 can be useful in making comparisons with subsequent measured signatures by the sensors 92 to determine particular contaminants or deterioration.

The first deterioration plot 204 can be representative of a measurement of the lubricant 170 having 20-40% deterioration. Noticeably, the first deterioration plot 204 differs from the baseline plot 202 and includes a greater amount of absorbance. Such differences can be compared and analyzed by the processor 166 to determine that the 20-40% deterioration has occurred. Such information can be communicated in real-time to the aircraft, display 176, or other remote monitor.

Similarly, the second deterioration plot 206 can be representative of a measurement of the lubricant 170 having 40-60% deterioration. Here, the plot 206 differs from the signature in the baseline plot 202, having a greater shift from the baseline plot 202 than that of the first deterioration plot 204. Again, such information can be communicated in real-time.

Next, the oil slag or oil varnish plot 208 can be representative of the Raman Spectroscopy signature that can identify the existence of oil slag or varnish within the lubricant 170. As opposed to comparing the oil varnish plot 208 to the baseline plot 202, other particular indicators can be stored in the memory 168 of the controller 164, which can identify particular aspects of the Raman spectroscopy signature to indicate the particular contamination; namely oil varnish as in the oil varnish plot 208. For example, a large portion of the wavenumber for the oil slag or varnish plot 208 is decreasing as the wavenumber increases, as opposed to that of the oil deterioration. The memory 168 can store a multitude of different signatures for use the by processor to determine a particular contamination type, level of contamination, contamination intensity, or level of deterioration based upon measurements of the sensors 92.

Lastly, the oil coking plot 210 can be representative of a Raman signature for an oil coke-type contamination. The oil coking plot 210 also decreases as the wave number increases, but different than that of the oil varnish plot 208. As such, communicating this signature to a controller can allow identification of the particular type of contamination, or level of deterioration.

It should be understood that any type of contamination or deterioration can be stored in the controller, and that measurement of a Raman signature by one or more sensors 92 can be used to determine a contamination type or level of deterioration. Such determination can be made by a controller, such as by way of comparison of a measured signature to a known signature, in one non-limiting example.

Figure 5:
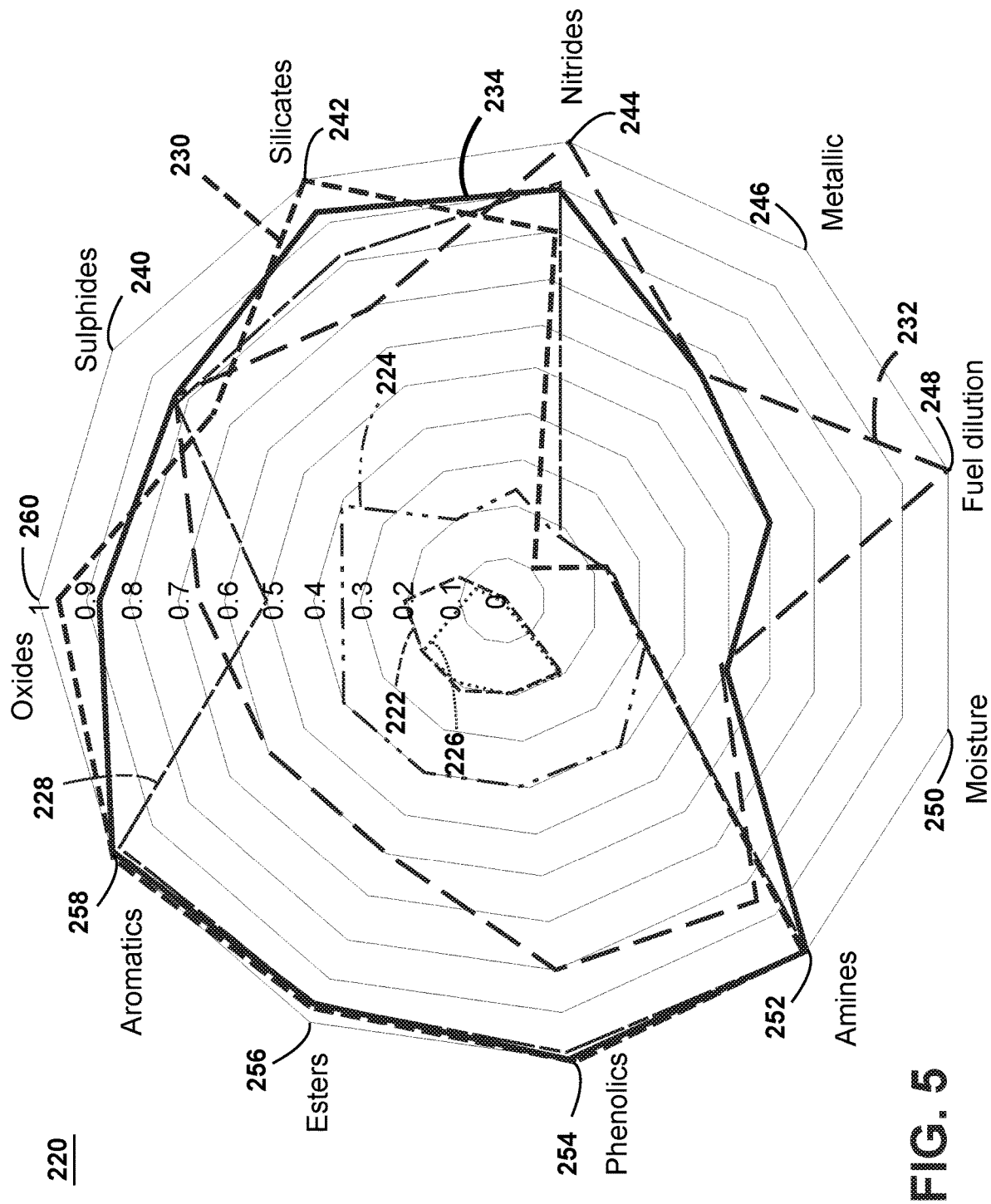
FIG. 5 is another plot graph illustrating data representative of different lubricant contamination as determined by readings from the sensors of FIG. 3.

Referring now to FIG. 5, another exemplary type of signature is illustrated as a contamination plot 220. The contamination plot 220 is shown in a hendecagonal, or eleven-sided polygonal organization, with each corner representative of a different exemplary, measurable chemistry or aroma component. Seven different contamination types are plotted on the contamination plot 220, as 10-20% deterioration 222, 30-40% deterioration 224, baseline 226, oil coking 228, oil varnish 230, fuel contamination 232, and dust contamination 234. Each contamination type can be representative of a combination of measured units in an aroma sensed by the sensors 92 that can be used to determine the particular type of contamination. The measured units, measured by the sensors 92, can include sulphides 240, silicates 242, nitrides 244, metallic 246, fuel dilution 248, moisture 250, amines 252, phenolics 254, esters 256, aromatics 258, and oxides 260, while alternative units are contemplated.

The contamination plot 220 is arranged in ten levels, each level being representative of normalized 10% content of a measureable unit up to a normalized 100% detection. It should be appreciated that 100% is not limited to the total of the combination or all measurable units, but representative of each individual unit on a normalized scale particular to aroma measurement.

For example, the 30-40% deterioration 224 can include a 40% measurement of sulphides 240, a 20% measurement of silicates 242, about a 24% measurement of nitrides 244, about an 18% measurement of metallic 246, about a 24% measurement of fuel dilution 248, about a 32% measurement of moisture 250, about a 40% measurement of amines 252, about a 40% measurement of phenolics 254, about a 40% measurement of esters 256, about a 40% measurement of aromatics 258, and about a 35% measurement of oxides 260. When a measurement of an aroma by the sensors 92 nears or matches these values in comparison by the controller 264, a determination that 30-40% deterioration of the lubricant has occurred. Nears or matches can mean that the measurements of the aroma by the sensors 92 can slightly differ from a compared contamination type or deterioration. For example, the values for some of the measurable units may be slightly off from the requirements for the particular type of contamination, such as +/−10% for a particular unit of measurement. Alternatively, one measurement unit of the whole can be farther off than the others, if the others are close. For example, if a measurement for eight of the nine measurement units is with 5%, but a final measurement unit is off by 20%, a determination of that contamination type can still be made.

It should be appreciated that a multitude of values used to determine the different types of contamination, the intensity of the contamination, or the level of deterioration can be stored in the memory 168 for comparison by the processor 166. Any number or different type of measurable units can be included to facilitate identification of the contamination or deterioration and should not be limited to the types of units or the types of contamination or deterioration as shown.

Furthermore, the values representative of the contamination or deterioration can be modified based upon an initial measurement or baseline. For example, if the sensors 92 measure a lubricant prior to operation of the engine 10 and determine a 10-20% deterioration, the processor 166 can determine that a real-time deterioration of 10-20% during operation can total a 20-40% deterioration, which can be signal that the lubricant should be changed or that there is a need for increased operational filtering.

Figure 6:
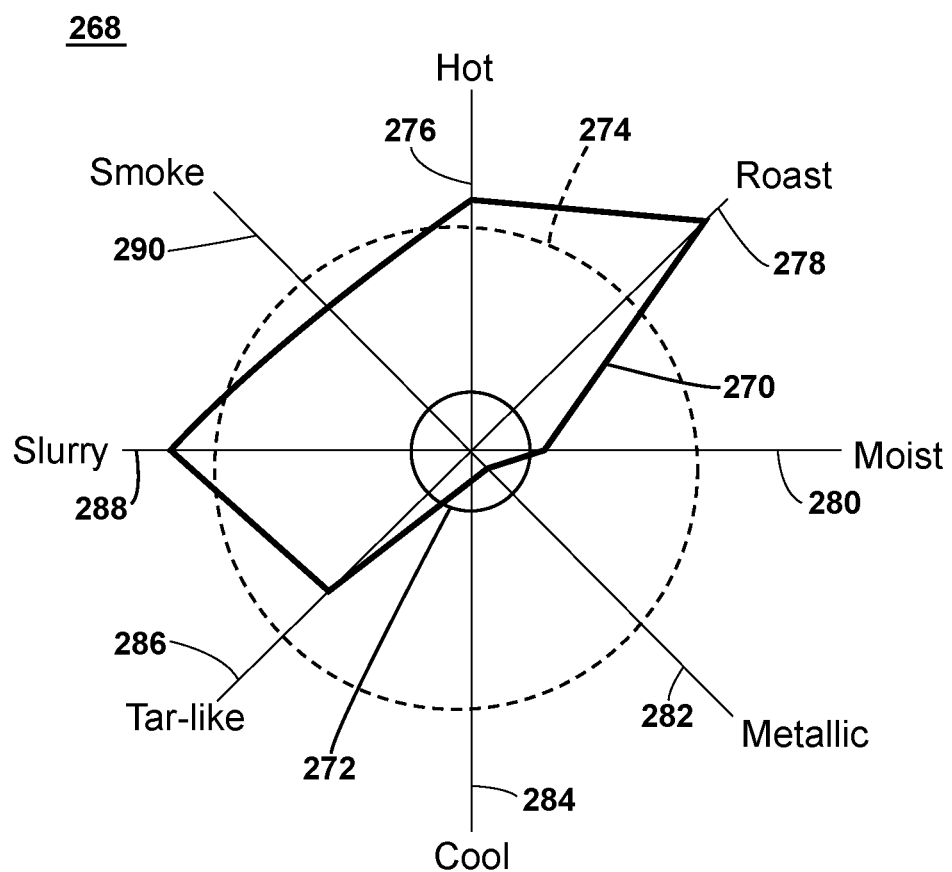
FIG. 6 is yet another plot graph illustrating minimum and maximum thresholds for the lubricant, and a plot showing an exemplary measurement by the sensors of FIG. 3 having sensed aspects above a maximum threshold.

Referring now to FIG. 6, each contamination type can further include an aromatic contamination profile 268 dedicated to the particular contamination type. An oil coking profile plot graph 270 can include a minimum threshold 272 and a maximum threshold 274 value for measured units for particular types of aromatics, including hot 276, roast 278, moist 280, metallic 282, cold 284, tar-like 286, slurry 288, and smoke 290. While shown as aromatics, any suitable measurable unit is contemplated. It should be appreciated that the particular aromatics as shown are exemplary, and any aromatics or measurable units by the sensors can be used. Non-limiting examples of aromatics can include warm, tingling, itching, metallic, cool, sharp, pungent, hot, roast, moist, cold, tar-like, slurry, smoke, or burning. As shown, the values for the slurry 288, hot 276, and roast 278 aromatics are above threshold levels, indicating that oil coke formation may have begun. Such aromatics measured by the sensors 92 can be communicated to the controller 164 as a generated signal to compare with the threshold values 272, 274. The controller 164 can then act based upon such measurements, such as sending or reporting the contamination to the display 176. When all values remain within the minimum and maximum thresholds 272, 274, the controller 164 can determine that no oil coking has begun to occur.

Figure 7:
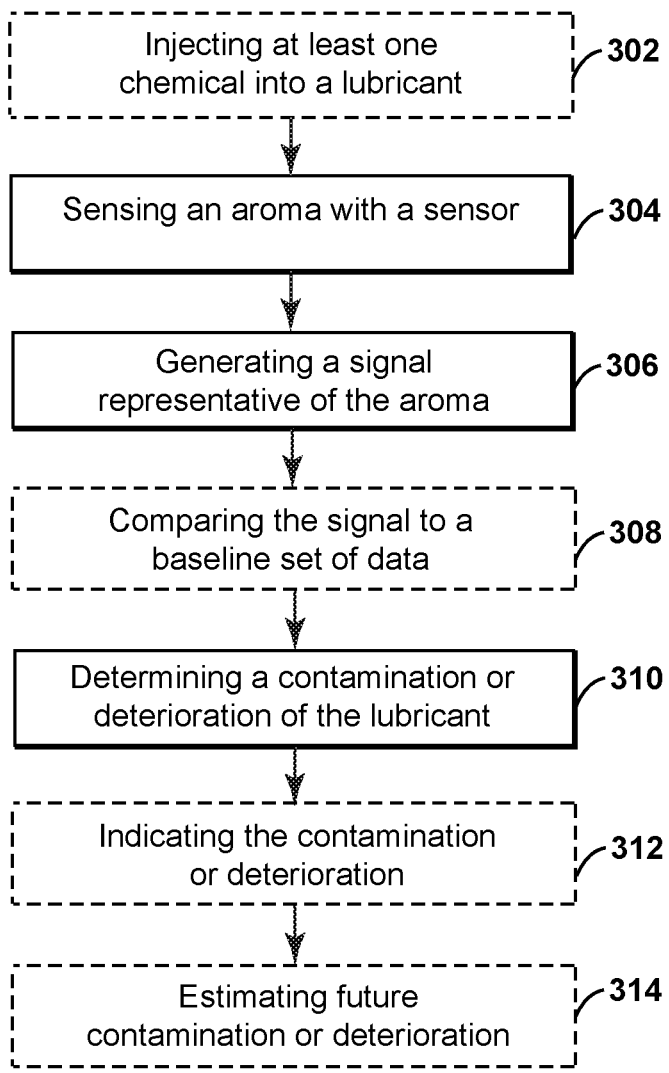
FIG. 7 is a flow chart illustrating a method of determining contamination in a vehicle lubrication system.

Referring now to FIG. 7, a method 300 for determining contamination in a vehicle lubrication system, such as the lubricant flow system 88 described herein, can include: at 304, sensing an aroma of a lubricant in a vehicle lubrication system with at least one sensor; at 306, generating a signal with the at least one sensor representative of the sensed aroma; and, at 310, determining, with a controller, a contamination or deterioration of the lubricant based on the signal representative of the sensed aroma. The vehicle lubrication system can be provided in an on-wing, aircraft turbine engine, such as the engine 10 of FIG. 1, for making real-time or in-flight measurements.

The method 300 can optionally include, at 302, injecting, with an injector, such as the injector 172 of FIGS. 2 and 3, at least one chemical to the lubricant before sensing the aroma. Injecting another chemical can be useful in improving or tailoring the measurements of the sensors. In one example, Sulphur can be injected by the injector to form hydrogen sulphide or thiols, which can improve detectability or measurability by the sensors.

At 304, sensing the aroma of a lubricant can be measured by sensing with the sensors 92 as described herein. Non-limiting exemplary sensors can include Raman spectroscopy, X-ray spectroscopy, infrared sensors, or laser wavelength sensors. Sensing with the sensor can include sensing one or more of sulphides, oxides, olefins, alkanes, nitrides, cycloalkanes, aromatics, asphaltenes, silicates, amines, esters, phenolics, or metallics in non-limiting examples. Additionally or alternatively, the sensor can sense aromatics such as warm, tingling, itching, metallic, cool, sharp, pungent, or burning in further non-limiting examples. The sensor can be positioned on a lubricant reservoir or a heat exchanger, such as the lubricant reservoir 90 or the heat exchangers 120, 122, 126 as described herein, while any desirable position is contemplated.

At 306, the at least one sensor can generate the signal, which can be a data set representative of the measurements of the sensor. For example, the signal can be in the form of the Raman signature of FIG. 5. In another example, the signal can be in the form of one or more measured values for the sensed aroma.

The method 300 can optionally include, at 308, comparing the signal to a set of baseline data with the controller. The processor 166 in the controller 164 can be used to compare measurements with stored data to determine if the contamination or deterioration has occurred. The stored data, such as the baseline data or threshold data can be stored in the memory 168, for example. Such baseline or threshold data can be representative of a particular contamination type, contamination intensity, or deterioration level.

At 310, the method 300 includes determining with the controller, such as the controller 164 as described, the contamination or deterioration can be based on the signal generated by the sensor. The controller, for example, can compare the signal to a baseline data set or threshold data set to determine if the aroma is representative of the contamination or deterioration. The baseline or threshold data set can be representative of a contamination type, contamination intensity, or deterioration level. Particular contamination types can include, in non-limiting examples, oil coke, oil varnish, oil slag, fuel, free-on-board oil, water, dust, dirt, ice, or sand. Determining can further include logging the contamination or deterioration determination. Additionally, determining could include determining service data, such as a service interval, service schedule, or that service is required. Additionally, particular contamination types could be tailored to particular determinations. For example, determining a fuel contamination could include determining a fuel maintenance or service schedule.

At 312, the method 300 can optionally include indicating the contamination or deterioration of the lubricant by the controller 164. After determining the contamination or deterioration of the lubricant, the controller 164 can indicate the contamination or deterioration, such as with the wireless communication link 174 of FIG. 2. Such an indication can be shown on the display 176, for example, by outputting a signal to the display 176. In one non-limiting example, the display 176 can be a mobile display, such as a mobile handheld device or a display provided within the vehicle, such as an aircraft carrying the vehicle lubrication system. Indicating can further include displaying the particular determination, such as the service data, service interval, or service schedule.

At 314, the method 300 can optionally include estimating a future deterioration or contamination. Such estimations can include additional measurements, which may or may not be determined by the sensors, including usage time, vehicle location, or operational temperature. In a first example, the sensed aroma can be measured in combination with a usage time. An increased usage time can coincide with a greater level of deterioration of the lubricant. In a second example, the sensed aroma can be measured in combination with a vehicle location. Operation of the vehicle in a sandy or desert environment can coincide with a greater risk of sand-type contamination, for example. In a third example, the sensed aroma can be measured in combination with operational temperature of the vehicle, engine, or lubrication system. Increased operational temperatures can coincide with a greater rate of deterioration, for example. Such additional measurements can improve determination of the contamination or deterioration of the lubricant as well as provide for improved models for future contamination or deterioration determinations. Estimations can further include determining a lubricant lifetime or a service model for the vehicle lubrication system. The determination can predict lubricant lifetime based upon anticipated usage times or operational temperatures. Additionally or alternatively, the determination can also anticipate or predict particular contamination types based upon operational environment, such as sandy locales, in one example.

The aspects as described herein provide for improved monitoring of lubricant life and contamination. Lubricant deterioration like oil coking, varnish, and slag can be more readily identified or predicted. Additionally, lubricant contamination can be more readily identified and issues with the lubricant system can be more readily identified. Furthermore, real-time, reliable online monitoring is possible, and traditional ineffective method for monitoring or maintenance of lubricant are reduced or eliminated. Further still, utilizing the sensors as described herein can provide for automatic lubricant monitoring, without requiring interval inspection to determining contamination or deterioration. Improved lubricant monitoring and performance can lead to improved engine efficiency and reduced maintenance, which can decrease overall costs.

Additionally, it is further contemplated that overall engine maintenance can be improved, beyond just lubricant maintenance and schedule. Particularly, gears, bearings, sumps, diagnostics, or other engine sections lubricated, cooled, or otherwise related to the vehicle lubrication system can be identified through contamination or deterioration detectable with the sensors. As such, maintenance of the engine beyond simply lubricant change and schedule is contemplated. The monitoring of the sensors as described herein can include a wide range of engine monitoring by identifying the contamination, deterioration, or change in the lubricant.

It should be appreciated that application of the disclosed design is not limited to turbine engines with fan and booster sections, but is applicable to turbojets and turbo engines as well. Further still, such disclosures are applicable to other lubricant systems and vehicles.

To the extent not already described, the different features and structures of the various embodiments can be used in combination, or in substitution with each other as desired. That one feature is not illustrated in all of the embodiments is not meant to be construed that it cannot be so illustrated, but is done for brevity of description. Thus, the various features of the different embodiments can be mixed and matched as desired to form new embodiments, whether or not the new embodiments are expressly described. All combinations or permutations of features described herein are covered by this disclosure.

This written description uses examples to describe aspects of the disclosure described herein, including the best mode, and also to enable any person skilled in the art to practice aspects of the disclosure, including making and using any devices or systems and performing any incorporated methods. The patentable scope of aspects of the disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for determining contamination in a vehicle lubrication system, the method comprising:
 sensing an aroma of a lubricant in the vehicle lubrication system with at least one sensor;
 generating a signal, from the at least one sensor, representative of the aroma; and
 determining, with a controller, a contamination of the lubricant based on the signal representative of the aroma;
 wherein the contamination is one of oil coke, oil varnish, oil slag, free-on-board oil, water, dust, dirt, ice, or sand.

2. The method of claim 1, further comprising indicating, by the controller, that the contamination has been determined.

3. The method of claim 2 wherein the indicating includes the controller outputting the signal to a display.

4. The method of claim 3 wherein the display is on an aircraft that includes the vehicle lubrication system.

5. The method of claim 1 wherein the determining further comprises comparing the signal to a threshold value to determine the contamination.

6. The method of claim 5 wherein the threshold value is representative of a contamination type or a contamination intensity.

7. The method of claim 1 wherein sensing the aroma includes sensing one or more of sulphides, oxides, olefins, alkanes, nitrides, cycloalkanes, aromatics, asphaltenes, silicates, amines, esters, phenolics, or metallics.

8. The method of claim 7 wherein sensing the aroma includes sensing one or more of the sulphides, oxides, olefins, alkanes, nitrides, cycloalkanes, aromatics, asphaltenes, silicates, amines, esters, phenolics, or metallics by determining the aroma as one or more of metallic, sharp, pungent, roast, tar-like, smoke, or burning.

9. The method of claim 1 wherein the vehicle lubrication system is provided in an on-wing, aircraft turbine engine.

10. The method of claim 1, further comprising estimating a future contamination of the lubricant based upon the determined contamination and at least one of a usage time of the lubricant, a vehicle location of a vehicle within which the vehicle lubrication system exists, or an operational temperature of the lubricant.

11. The method of claim 10, further comprising determining a lubricant lifetime or a service model for the vehicle lubrication system based upon estimating the future contamination.

12. The method of claim 1 wherein the sensing uses one of Raman spectroscopy, X-ray spectroscopy, infrared, or laser wavelengths.

13. The method of claim 1, further comprising injecting, with an injector, at least one chemical to the lubricant before the sensing the aroma.

14. The method of claim 13 wherein the at least one chemical is sulfur, an alcohol, a carboxylic acid, an aldehyde, or a ketone.

15. A method for determining oil degradation and a type of oil degradation in a vehicle lubrication system, the method comprising:

sensing an aroma of a lubricant in the vehicle lubrication system with at least one sensor;

generating a signal, from the at least one sensor, representative of the aroma; and determining, with a controller, an oil degradation and a type of oil degradation of the lubricant based on the signal representative of the aroma;

wherein the type of oil degradation is one of oil slag, oil coke, or oil varnish.

16. The method of claim 15 further comprising determining a service schedule for the vehicle lubrication system based upon the oil degradation and indicating, on a display, the service schedule.

17. The method of claim 15 further comprising storing historical data representative of the type of oil degradation and determining a service model for the vehicle lubrication system based upon the historical data.

18. A method for determining contamination in a vehicle lubrication system, the method comprising:

sensing an aroma of a lubricant in the vehicle lubrication system with at least one sensor;

generating a signal, from the at least one sensor, representative of the aroma; and determining, with a controller, a contamination of the lubricant based on the signal representative of the aroma;

wherein the contamination is one or more of fuel, water, dirt, dust, sand, ice, organic material, metals, or ceramics.

* * * * *